(12) United States Patent  (10) Patent No.: US 9,079,735 B2
Haas  (45) Date of Patent: Jul. 14, 2015

(54) ANTI-STICK HISTOLOGICAL SPECIMEN SLIDE FEEDER AND METHOD

(71) Applicant: Primera Technology, Inc., Minneapolis, MN (US)

(72) Inventor: Darren W. Haas, Minnetonka, MN (US)

(73) Assignee: Primera Technology, Inc., Minneapolis, MN (US)

( * ) Notice: Subject to any disclaimer, the term of this patent is extended or adjusted under 35 U.S.C. 154(b) by 101 days.

(21) Appl. No.: 13/750,215

(22) Filed: Jan. 25, 2013

(65) Prior Publication Data
US 2014/0212256 A1   Jul. 31, 2014

(51) Int. Cl.
| B65H 3/48 | (2006.01) |
| B65H 3/12 | (2006.01) |
| B41J 3/407 | (2006.01) |
| B41J 13/10 | (2006.01) |
| B65H 3/06 | (2006.01) |
| B01L 3/02 | (2006.01) |
| G01N 1/31 | (2006.01) |
| G01N 35/00 | (2006.01) |

(52) U.S. Cl.
CPC . *B65H 3/48* (2013.01); *B41J 3/407* (2013.01); *B41J 13/103* (2013.01); *B65H 3/063* (2013.01); *B65H 3/128* (2013.01); *B01L 3/0241* (2013.01); *G01N 1/312* (2013.01); *G01N 2035/00861* (2013.01)

(58) Field of Classification Search
USPC .......... 221/259, 268, 270, 277, 278; 271/104, 271/105, 12, 195, 90, 97, 98; 406/90; 414/796.5, 796.6, 796.9, 797, 797.4, 414/797.6, 797.7, 797.8, 797.9
See application file for complete search history.

(56) References Cited

U.S. PATENT DOCUMENTS

| 4,171,131 | A | * | 10/1979 | Stange et al. | 271/236 |
| 4,823,535 | A | * | 4/1989 | Schmidt et al. | 53/284.4 |
| 5,167,407 | A | * | 12/1992 | Namba | 271/98 |
| 5,562,402 | A | * | 10/1996 | Muto | 414/797.7 |
| 6,951,663 | B1 | * | 10/2005 | Edwards | 427/2.11 |
| 7,637,713 | B1 | * | 12/2009 | Parette | 414/795.5 |
| 8,013,884 | B2 | * | 9/2011 | Schlinkmann et al. | 347/171 |

FOREIGN PATENT DOCUMENTS

JP         58162442 A  *  9/1983  ........... B65G 59/04

* cited by examiner

*Primary Examiner* — Gregory Adams
(74) *Attorney, Agent, or Firm* — Faegre Baker Daniels LLP (57) ABSTRACT

An apparatus and method for feeding histology specimen slides from a stack of the slides in a slide printer. The stack of slides includes first, next-to-be removed and second slides having adjacent surfaces. A flow of gas is applied to a location that the adjacent surfaces of the first and second slides meet when removing the first slide from the stack. The flow of gas, which may be a jet or blast of air applied through a nozzle, and which may be applied before and/or during the removal of the slide from the stack, helps un-stick the slides to enhance the feeding action.

19 Claims, 11 Drawing Sheets

ANTI-STICK HISTOLOGICAL SPECIMEN SLIDE FEEDER AND METHOD

BACKGROUND

The invention relates generally to histological specimen slide printers. In particular, the invention is a system and method for feeding histological specimen slides from a stack of such slides into a printer.

Printers for printing information on containers such as slides used to process histological specimens (e.g., tissue biopsies) are generally known and commercially available. Printers of these types are, for example, disclosed in PCT International Application Publication Nos. WO 2012/036865 having an international filing date of Aug. 25, 2011 and WO 2012/036874 having an international filing date of Aug. 26, 2011, both of which are incorporated herein by reference in their entirety and for all purposes. Stacks of the slides with their major surfaces in contact with the major surfaces of adjacent slides are loaded into the printers. A feeding mechanism removes individual slides from the stack and moves the slides toward the printhead during printing operations. Adjacent slides sometimes stick together and interfere with the proper operation of the feeding mechanism or other portions of the printer.

There remains a continuing need for improved histological slide feeders and methods. In particular, there is a need for feeders and methods that efficiently and effectively feed slides from a stack without complications associated with the slides sticking to one another.

SUMMARY

The invention is an improved slide feeder and method. One embodiment is a method for feeding histology specimen slides from a structure supporting a stack of the slides in a slide printer. The method includes: providing a stack of slides, including first and second slides having adjacent surfaces; removing the first slide from the stack; and applying a flow of gas to a location that the adjacent surfaces of the first and second slides meet when removing the first slide from the stack. The flow of gas, which may be a jet or blast of air applied through a nozzle, and which may be applied before and/or during the removal of the slide from the stack, helps un-stick the slides to enhance the feeding action.

DETAILED DESCRIPTION

A histological specimen slide cartridge 18 in accordance with one embodiment of the invention is shown in FIGS. 1-2, 6-7 and 10-19. Slide cartridge 18 can be used in connection with a color slide printing system 10 shown generally in FIGS. 1-5. The slide printing system 10 includes an outer cabinet 12 in which components are mounted, and the cabinet includes a cross support wall 14 extending between and suitably supported on side walls 16. The side walls 16 are used for rotatably supporting various drive rollers and other components. Medical slide cartridge 18 (also sometimes referred to as a cassette or magazine) is a rectangular container that holds a plurality of individual slides 100. The slides 100 can be of a desired type, and can be clear or opaque and they will have a finish on at least portions of one surface that will accept ink from a thermal printer that has a multi-colored ribbon. A frosted finish in the area to be printed is suitable.

The cartridge 18 is a self-contained unit that can be loaded with slides 100 from the bottom or can have a suitable access cover, and it can be slid in and out of the outer printer housing 12 through a provided opening, and between side guides (FIG. 1) and rested on the support wall 14. As can be seen, the cartridge size is selected to support a number of slides 100 in a stack (usually 100), and the bottom wall 22 of the cartridge 18 has a feed opening 24 defined therein formed, by terminating the bottom wall 22 so it is spaced from an inner or infeed end wall 25. The end wall 25 is terminated with a bottom edge 26 spaced slightly above the top plane of the bottom wall 22, so that when a cartridge 18 is positioned in the print housing, as shown in FIG. 2, an input feed roller 28 will support the bottommost slide 100 (the roller 28 projects above wall 14), and hold the end of the slide position so that the bottom slide will clear the bottom edge 26. The input feed roller 28 will withdraw the bottom slide 100 through the opening 24 when the feed roller is powered. The input feed roller 28 is driven by a suitable motor 32 from a central control system 34 which comprises a microcontroller that can be programmed for sequencing the various components being controlled in a desired manner and which coordinates the printing on the slide 100 for identification.

Provided slide guides 35 will support a slide 100 after it is moved by the input feed roller 28 underneath the wall edge 26, and the input feed roller 28 will provide an impetus to move the slide along the guides 35 until it is grasped by drive rollers indicated at 38 and 40. At least one of the drive rollers, for example drive roller 40 is driven by a motor 42 that is also controlled by the control system 34. The slide 100 being fed is grasped between the drive rollers 38 and 40 and is moved across a slide position sensor 37 onto a printer printhead platen roller 46 that is driven by a motor 48 from control system 34. The slide position sensor 37 provides a position signal to control system 34 so the drive rollers 38 and 40 are driven to properly position the slide 100 relative to the printhead.

Figure 5:
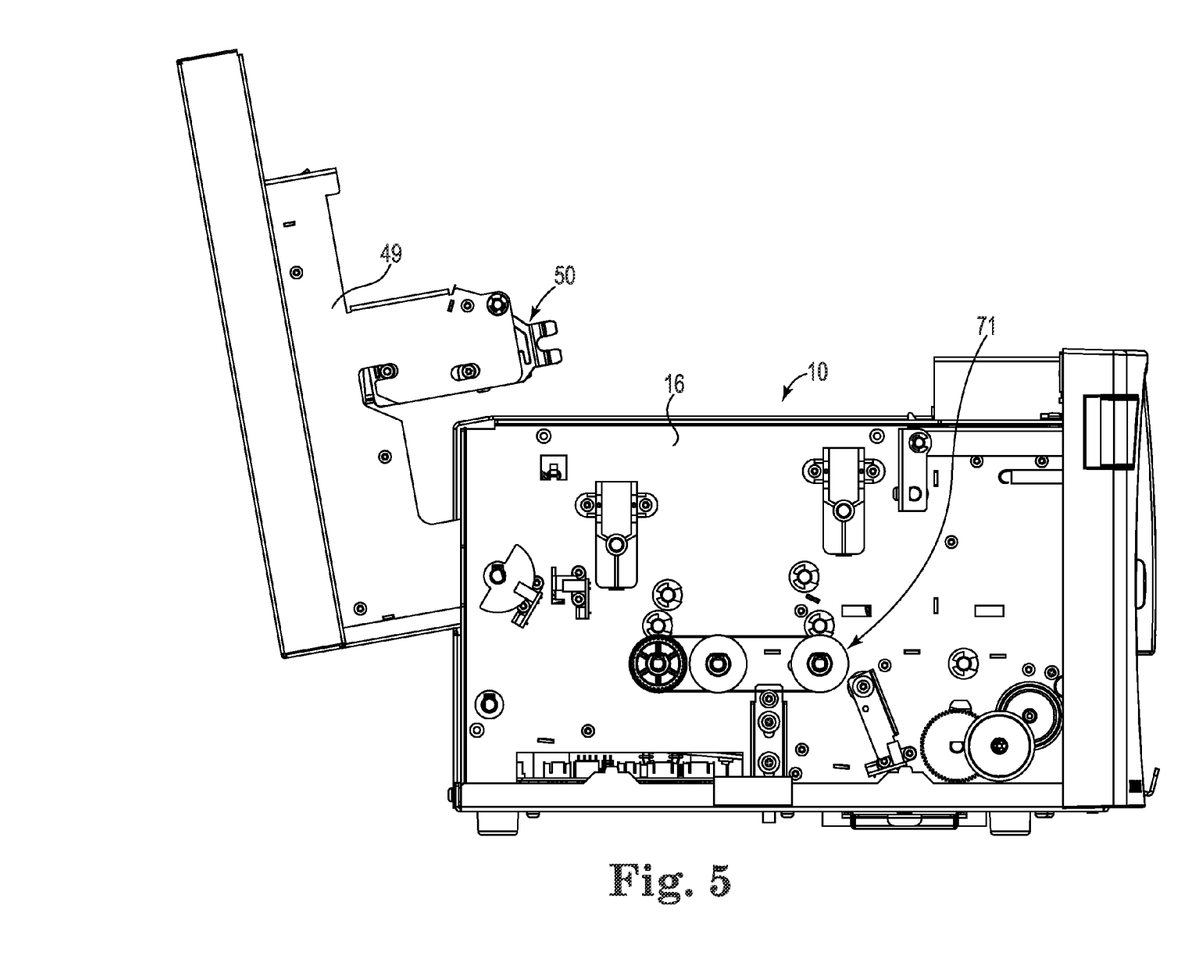
FIG. 5 is a side view of the printing system shown in FIG. 1, with a cover carrying the printer in an open position.

Printhead platen roller 46 is independently mounted between the side walls 16 of the housing, and above the platen roller there is a thermal printer indicated at 50 that includes a thermal printhead 52 that will print on an upper surface of a slide, for example, the slide 100A shown in FIG. 2 between the drive rollers 70 and 72 and supported on the printhead platen roller 46. The printer 50 is carried on a cover 49 that can be opened as shown in FIG. 5, and the printer is supported on the cover 49 for movement toward and away from printhead platen roller 46 when the cover 49 is closed. A lever 51 is pivoted at a pivot 51A and has an end finger 51B that engages a crossbar on the printer 50 frame. A cam 53 is positioned to act on a cam follower 51C on the lever 51 to lift the printer and printhead when the cam is rotated by a motor 55. The motor 55 is controlled by control system 34.

The slide 100A is moved beneath a multi-color thermal print ribbon indicated at 54 which is fed from a ribbon supply roller 56 mounted between the side walls 16 and which passes under the printhead 52. The print ribbon supply roller is driven by a suitable motor 59. The ribbon 54 is a known ribbon with blocks of heat transferable color along its length in a known sequence, namely yellow (Y), magenta (M), cyan (C) and black (K). The ribbon 54 passes across a print ribbon sensor 58 that provides signals indicating the start of each block of color on the ribbon to the control system 34. Guide rollers 57 are also provided for the ribbon 54 between the supply roller 56 and the printhead 52. The ribbon 54, after it has been used for printing onto the slide 100A, is taken up on a print ribbon take up roller 62, that can be driven with a suitable motor 64 controlled by the control system 34.

Prior to printing, the printhead 52 is raised by operating cam 53 to lift the printer and the slide 100A will be moved forwardly toward a pair of drive rollers 70 and 72 again, at least one of which is driven, for example by schematically illustrated motor 74 coordinated with the control system 34. It should be noted that while individual drive motors for the feed rollers and platen roller are shown for illustration purposes, the rollers that are timed or coordinated can be driven by one motor and a gear train shown generally at 71 in FIG. 5.

Figure 1:
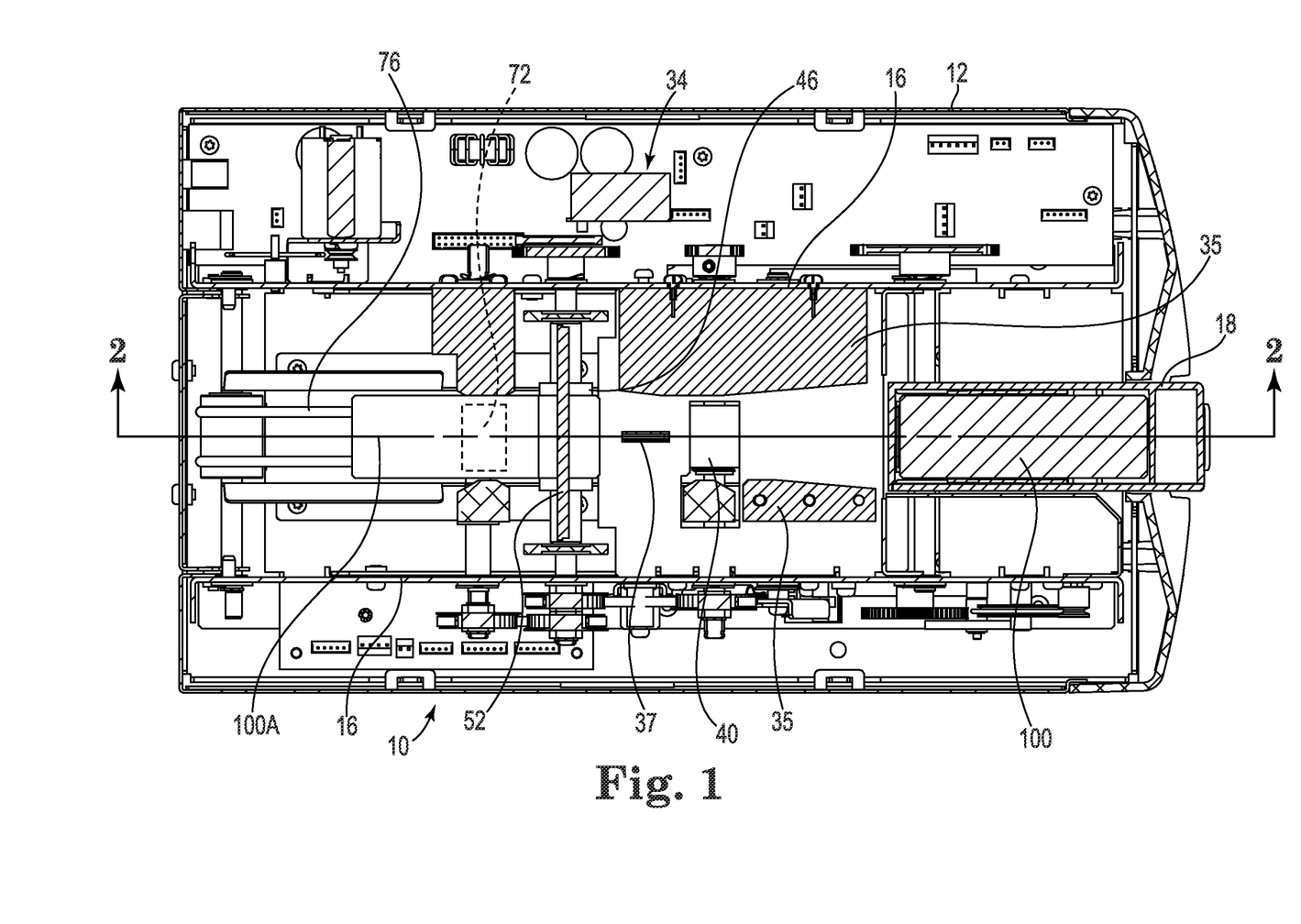
FIG. 1 is a top sectional view of a histological specimen slide printing system, taken on line 1-1 in FIG. 2
Figure 2:
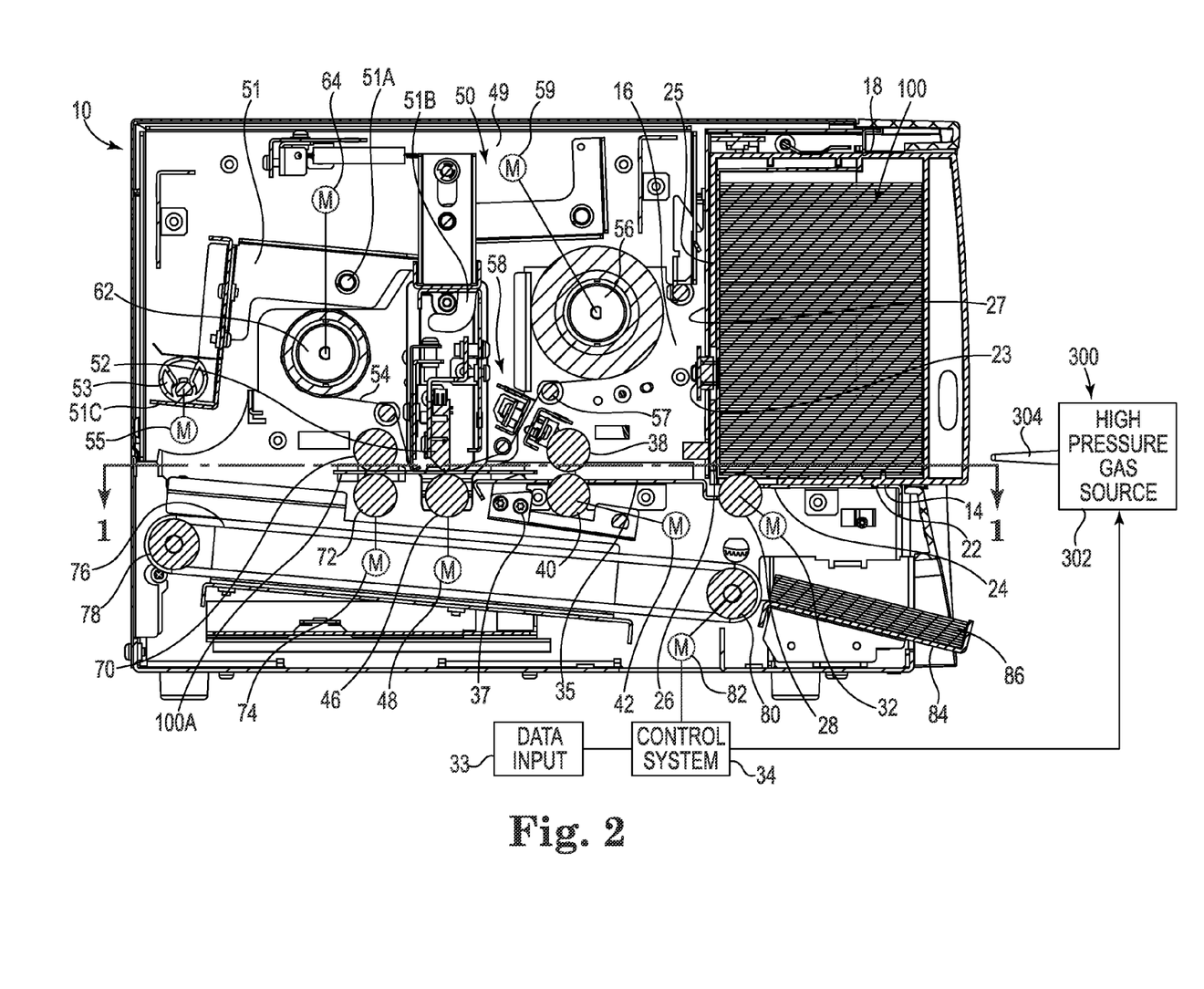
FIG. 2 is a sectional view of the slide printing system shown in FIG. 1, taken on line 2-2 in FIG. 1 and diagrammatically showing an anti-stick slide feeder in accordance with an embodiment of the invention.
Figure 3:
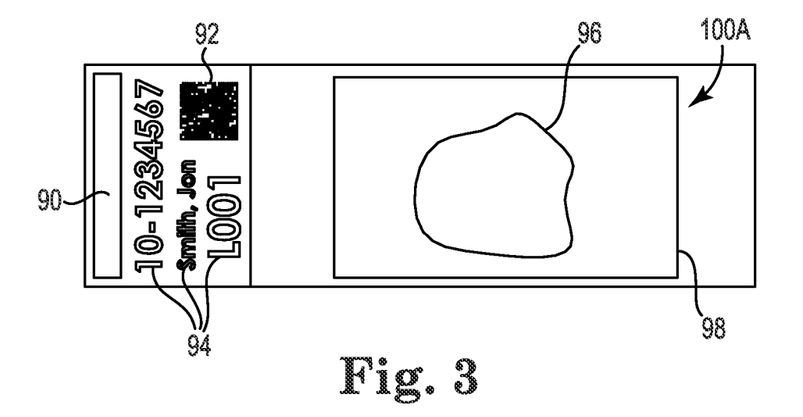
FIG. 3 is a top plan view of a slide fed and printed in accordance with one embodiment of the invention by the printing system shown in FIGS. 1 and 2.

As the slide 100A is printed (as shown in FIG. 1), it should be understood that it will be moved back and forth by drive rollers 70 and 72 and platen roller 46 under control of the control system 34. Printing occurs adjacent one end of the slide as shown in FIG. 3 so the drive rollers 70 and 72 are usable for moving the slide 100A while it is being printed on.

The printhead 52 has enough lateral width so that the printing can take place along the lateral width of the slide wide enough to include the information necessary. The printhead 52 is lifted when needed for moving the slide 100A to reposition it.

After the slide 100A has been printed by printing a colored bar 90 (See FIG. 3), a bar code 92 and identification text 94, the slide is driven through the drive rollers 70 and 72 under the power of motor 74, and it is dropped into a storage facility. In this form, the printed slide is dropped onto a conveyor belt 76 that is mounted over first and second end rollers 78 and 80. The end of the conveyor supported by roller 80 is located back underneath the slide cartridge 18. The roller 80 can be driven by a suitable motor 82 controlled by the control system 34, or can be driven by the gear train 71.

The printed slides carried on the upper length of the conveyor belt 76 will be dropped into a slide output tray or bin 84 that is mounted in a suitable manner at an incline underneath the slide holder cartridge 18. The slides that have been printed have been shown at 86 in a stack.

The cartridges 18 could be loaded with different types of slides if desired, for example, if a party wanted to use colored slides with a monochrome ribbon instead of color ribbon with white or clear slides, the slide cartridge allows the user to easily switch slide colors without handling the slides. Multiple cartridges could be used to store multiple colors, which can be easily identified and switched while keeping them dust and fingerprint free.

In use, the administrator of the company that was using the slide identification system of the present disclosure would set up some variables for their system, for example, an automated color selection where a particular color identifies a particular tissue. For example, liver tissue could be blue; kidney tissue could be green; heart tissue could be red; lung tissue could be black and so on. The data input 33 into the software of the control system 34 can be manually input or read from another source, and used to identify the type of slide that was to be printed, and also for each particular slide the data would include in the software the text that was to be printed and the identification bar code that is to be printed on the slide. Then, the software would automatically select the slide identification color, based on the input data and the printhead would be operated to print the strip or identifying block 90 on the one end portion of the slide such as that shown in FIG. 3, and then the data relating to the specimen that would be placed on the slide is printed as text 94 and bar code 92 for identification. This can be done in a black color, so the slide information would be in two colors.

The thermal printer permits the color identifier bar or block 90 to be printed easily in a selected color and then the information about the tissue sample on the slide can be printed in a different color, such as black.

The ability to print the identifying color for the type of tissue that would be placed on the slide at the same time that the bar code is placed on eliminates errors in identifying the color code to be used.

FIG. 3 illustrates a typical slide 100A after printing and mounting a specimen thereon having the identifying color bar 90 shown in one portion of the slide and the printed data 94, including a bar code 92 that is printed in black and adjacent to the color bar and with a specimen 96 that is keyed to the information on the slide mounted on the slide. The specimen 96 can be covered by a slip cover 98 and retained on the slide in a known manner where desired.

Figure 6:
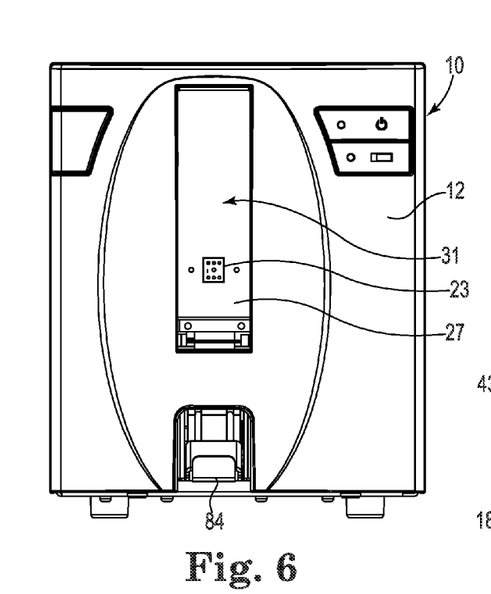
FIG. 6 is a front end view of the printing system shown in FIG. 1, with the slide cartridge removed.
Figure 7:
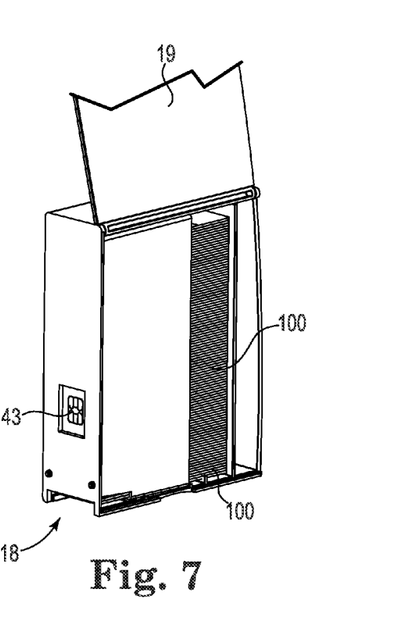
FIG. 7 is an isometric view of the slide cartridge shown in FIG. 1

FIG. 6 is a front end view of one embodiment of the printing system 10, with slide cartridge 18 removed from the cabinet 12 to show the cartridge receiving area 31. As shown, an electrical contact 23 is mounted on a wall 27 at the back of the cartridge receiving area 31. The electrical contact 23 is coupled to the control system 34. FIG. 7 is an illustration of a slide cartridge 18 with its access cover 19 open and showing the slides 100 stacked therein. The illustrated embodiment of the cartridge 18 has a memory chip 43 mounted to its back wall. The memory chip 43 is mounted to the cartridge 18 at a position that will enable the memory chip to electrically contact or otherwise be coupled for data transfer with the electrical contact 23 on the printing system 10 when the cartridge is inserted into the enclosure 12.

Figure 8:
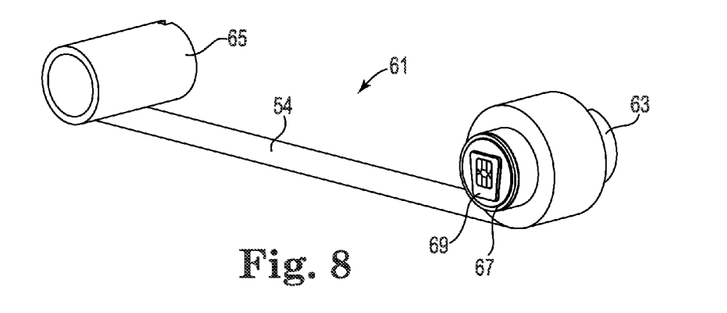
FIG. 8 is an isometric view of a print ribbon that can be used in the printing system shown in FIG. 1.
Figure 9:
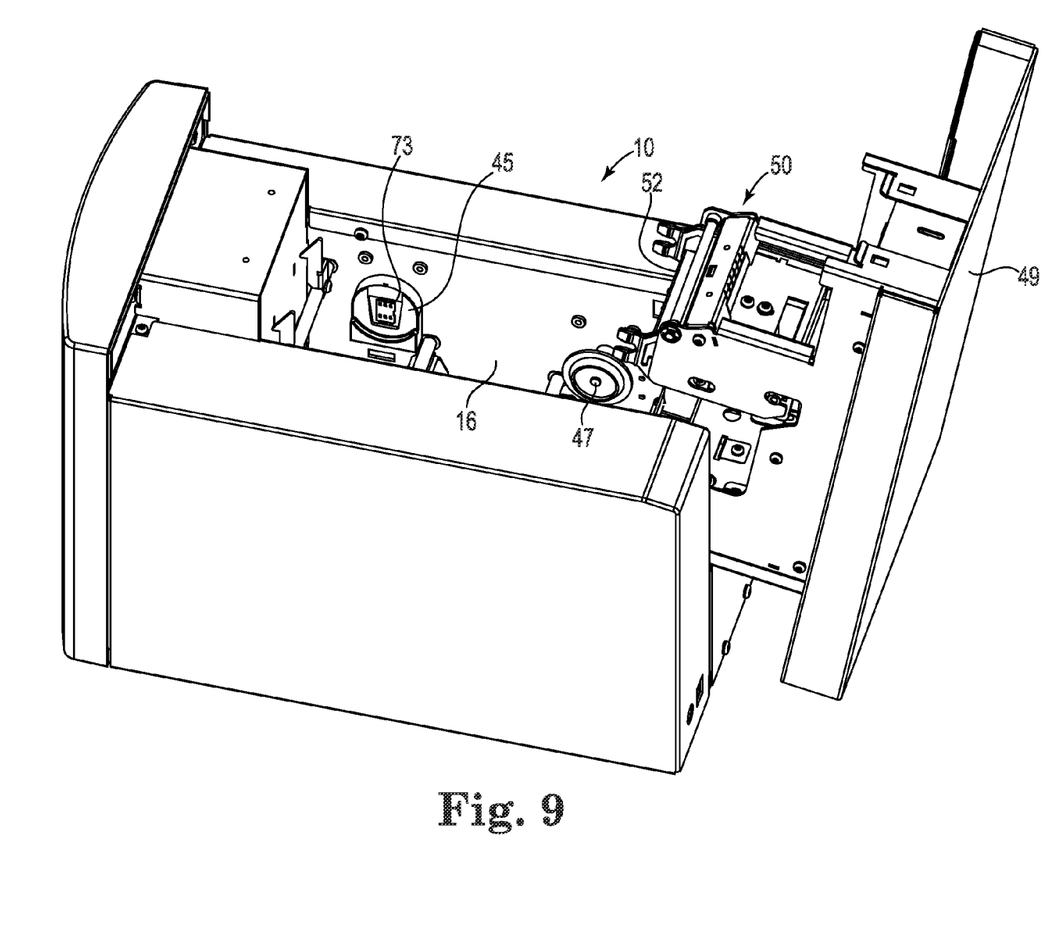
FIG. 9 is an isometric view of the printing system shown in FIG. 1 with the cover open.
Figure 10:
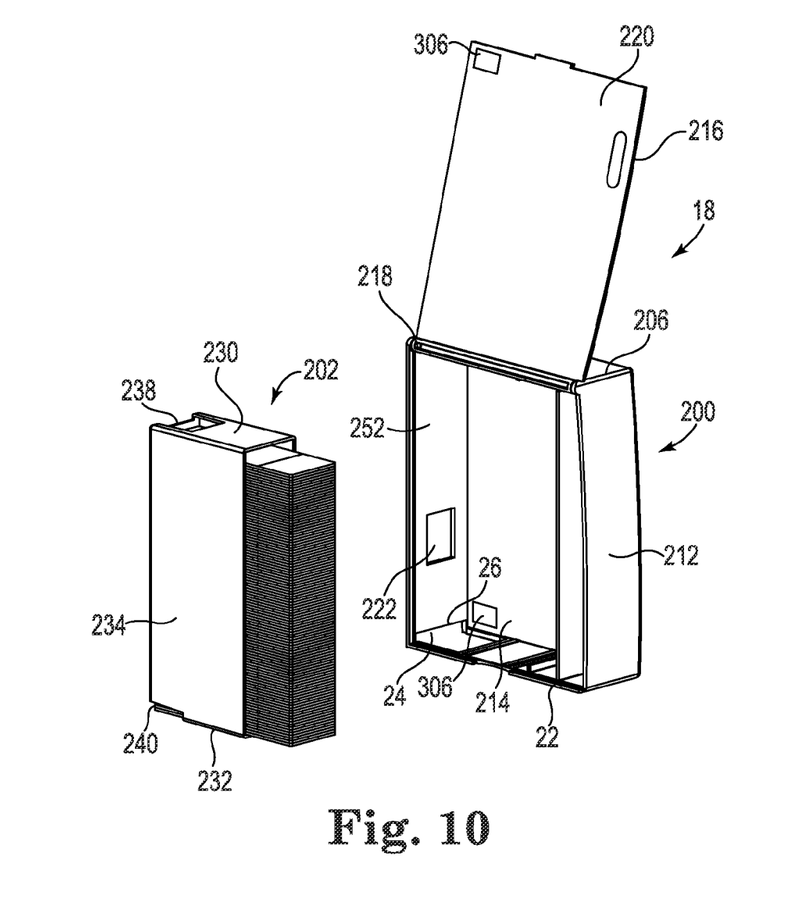
FIG. 10 is an exploded isometric view of a slide cartridge in accordance with one embodiment of the invention.
Figures 11, 12:
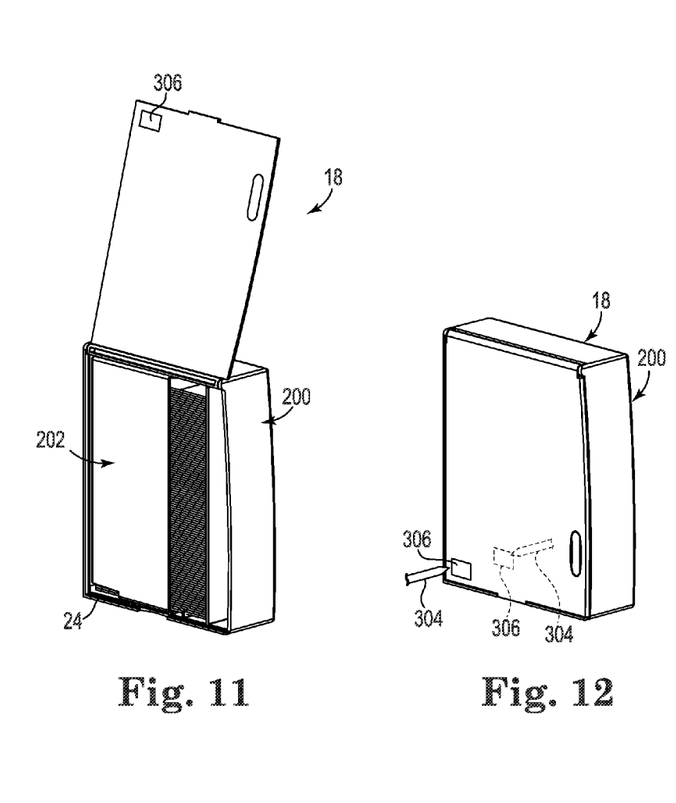
FIG. 11 is an isometric view of the cartridge shown in FIG. 10 with the slide holder positioned in the body and the access cover open.
FIG. 12 is an isometric view of the cartridge shown in FIG. 10 with the access cover closed and illustrating nozzles of the anti-stick slide feeder in accordance with an embodiment of the invention.
Figure 13:
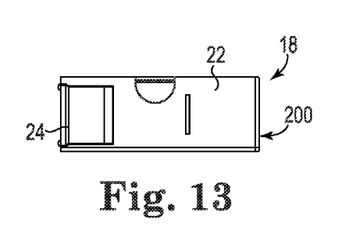
FIG. 13 is a plan view of the bottom of the cartridge shown in FIG. 10.
Figure 14:
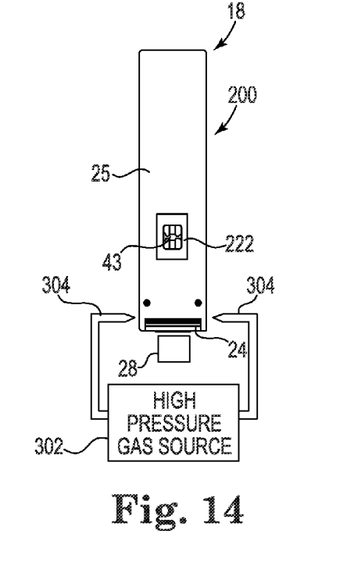
FIG. 14 is a plan view of an end of the cartridge shown in FIG. 10, showing the inner wall and diagrammatically illustrating the anti-stick slide feeder in accordance with an embodiment of the invention.
Figure 15:
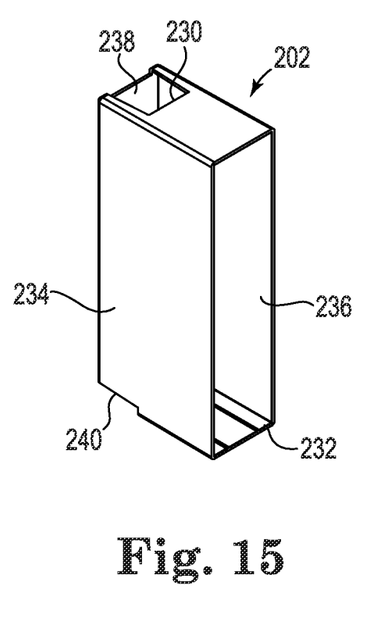
FIG. 15 is an isometric view of the slide holder of the cartridge shown in FIG. 10.
Figure 16:
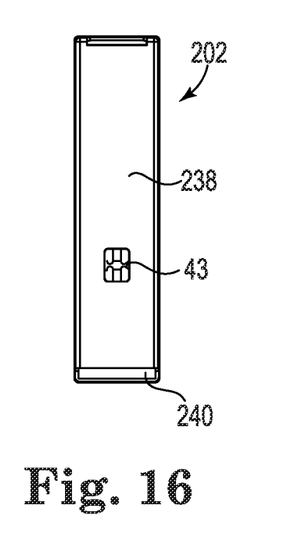
FIG. 16 is a plan view of an end of the slide holder shown in FIG. 15, showing the inner wall.
Figure 17:
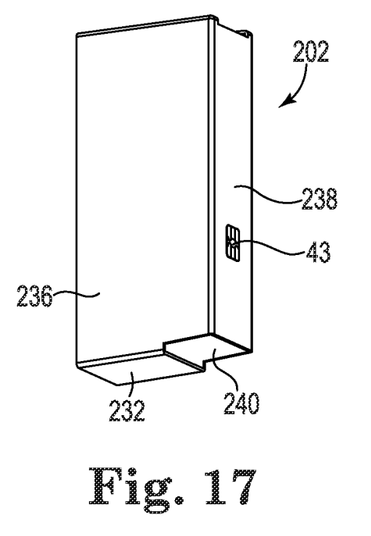
FIG. 17 is an isometric view of the slide holder shown in FIG. 15.

FIG. 8 is an illustration of a print ribbon assembly 61 that can be used with the slide printing system 10. As shown, the print ribbon assembly 61 includes supply spool 63, take-up spool 65, and multi-color thermal ink ribbon 54. The composition of thermal ink ribbons such as 54 is generally known. As described above, in one embodiment of the invention the ribbon 54 has a plurality of primary color ink blocks (e.g., yellow, magenta and cyan) and black ink blocks (not separately shown in FIG. 8) spaced in repeating sequences along its length. Rotatably mounted to the supply spool 63 is a hub 67. A print ribbon memory chip 69 is mounted to the hub 67 in this embodiment. FIG. 9 illustrates an embodiment of the printing system 10 where the print ribbon supply hub 45 includes an electrical contact 73 configured for electrical coupling to the memory chip 69 on the supply spool 63. The print ribbon assembly 61 is loaded onto the print ribbon receiving structure by mounting the supply spool 63 to the supply hub 45, and mounting the take-up spool 65 to the take up hub 47. The memory chip 69 on the supply spool 63 is electrically coupled to the ribbon supply chip contact 73 when the supply spool 63 is mounted to the supply hub 45.

When the printing system 10 is switched ON the control system 34 can access information on the slide cassette memory chip 43 through electrical contact 33, and can access information on the ribbon supply memory chip 69 through the electrical contact 73. Information stored on the slide cassette memory chip 43 can include, for example, one or more of slide type and the number of slides remaining in the cartridge 18. Similarly, information stored on the ribbon supply memory chip 69 can include ribbon type, the number of images remaining on the ribbon 54, production date and/or batch no. Other or additional types of information can be stored on memory chips 43 and 69 in other embodiments. Information on the memory chips 43 and 69 is used to control the operation of printing system 10, and can be updated after print operations. For example, if the information on memory chips 43 or 69 indicates that the supply of slides or ribbon is exhausted, the control system 34 will not execute a requested print operation. Information stored on memory chips 43 or 69 representative of the number of remaining slides and the number of images remaining on the ribbon 54 can be updated following each print operation. If the types of slides and print ribbon loaded into the printer are not compatible, the unsuitable combination can be identified and an informational message can be provided and/or printing can be discontinued to reduce errors.

In summary, the printer will have an input area that holds unprinted slides with a frosted area (typically white) used to record data. The slides will be contained in a cartridge that will hold slides. An input feed roller will drive one slide out of the cartridge and move it towards the printhead. A slide position sensor will locate the slide as it exits the cartridge and allow the controls to control the drive rollers to precisely locate the printable area of the slide under the printhead. The ribbon drive motor will then advance the multiple color panel ribbon until the leading edge of the first color panel of the sequence (typically yellow in a YMCK ribbon) is positioned under the printhead as well. A ribbon sensor detects the transition between the color blocks on the ribbon and allows the control system to indicate to the printer the location of each color block on the ribbon relative to the printhead. When both the slide and the ribbon are in the proper location, the printhead will be lowered and the drive rollers and the platen roller will advance the slide as the first color panel is printed. The printhead will be raised by a cam, the slide will back up until the leading edge is under the printhead and the color ribbon will be advanced until the leading edge of the next panel is under the printhead. Then the printhead will lower and the drive rollers will advance the slide as the second color panel on ribbon is printed. This process will repeat for the remaining color panels. Once all of the color panels have completed printing, the drive rollers will advance the slide until it exits the printhead area and is transferred to a conveyor belt which will move the slide to the output hopper located on the front of the machine directly under the input cartridge.

The data for the slide can either be manually entered at a computer or a histology tissue cassette with a bar code containing all pertinent information that can be scanned to obtain the required data to be reprinted on slides.

Figure 4:
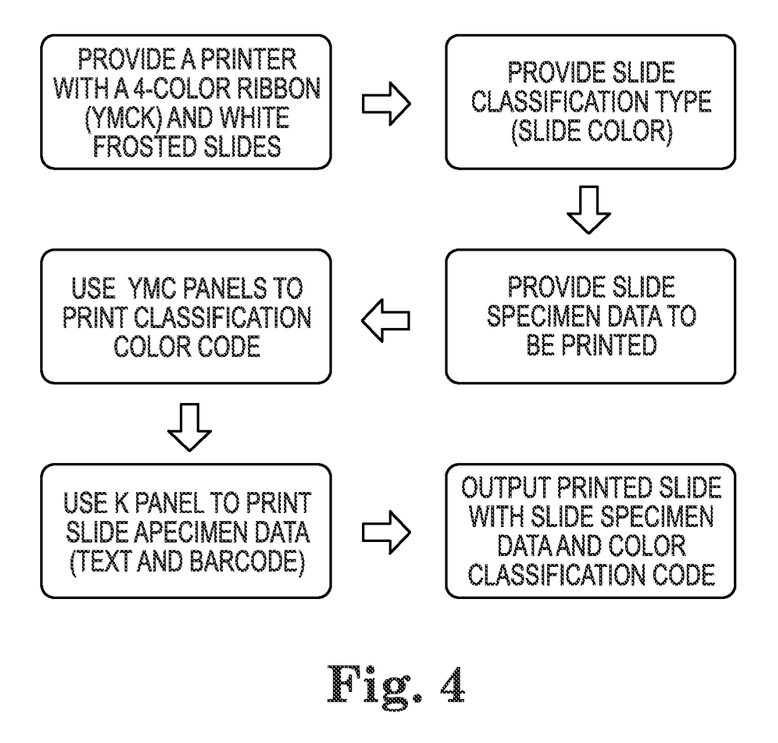
FIG. 4 is a block diagram of an operational sequence that can be used with the printing system shown in FIG. 1.

The sequence of operations in FIG. 4 shows the steps in the process using the colored ribbon for printing.

The printing system includes a cartridge for holding a number of medical slides or histological slides on which tissue samples or other medical samples are to be placed, and which will be provided to a printer that will print in color on the slide for further identification of the class of tissue or sample that is to be placed onto the slide, as well as printing information about the specimen on the slide. This includes printing a bar code and/or text containing the data necessary for use of the slide, such as case number, patient name, year, issue class, priority rating etc. The slides will be prepared with an ink receptive surface, such as frosting the areas where there will be printing.

The slides are loadable in a cartridge so that they can be handled without getting fingerprints or other debris on the slides themselves, and multiple cartridges can be used, each to store slides for a different classification of specimens to be mounted on slides. The cartridges then can be easily identified as to the class of the specimen and the cartridge switched while keeping the slides dust and fingerprint-free.

The printer utilizes a series of drive rollers for carrying slides individually from the cartridge, and feeding them into a print station that includes a platen roller that supports the slide for printing and a printhead that prints the information on a surface opposite from the platen roller. The slide can be moved back and forth by suitable drive rollers for multi-color printing, or black and white printing, and when the information has been printed into the slide, the slide is removed from the print station (the printhead is lifted away from the slide as it is moved for printing and out of the print station) and then the slide is transferred to an output bin. The finished slide transfer device includes a conveyor belt that will receive the slides and transport the printed slides to a bin. Other types of storage can be provided as well.

The printhead is controlled by suitable software that will print an identifying color mark, in a bar or strip form onto the slide, and then the data that is required, including a text and the bar code for identification is printed on the slide, and this is generally done in black printing. A control system is used for coordinating various movements with the printing operations, including controlling the lifting and lowering of the printhead, the motors for the slide drive rollers, and the platen roller for multiple pass printing to print the desired identification information on the slide.

Cartridge 18 can be described in greater detail with reference to FIGS. 10-19. As shown, cartridge 18 includes a body 200 and a slide holder 202. The body 200 is an enclosure configured to releasably slide into the printer, and in the illustrated embodiment includes top wall 206, bottom wall 22, inner end wall 25, outer wall 212 and side walls 214 and 216. Side wall 216 is formed as an access cover 220 and is mounted to top wall 206 by hinge 218. An opening for receiving the slide holder 202 is located in the side wall and can be enclosed by the cover 220. A memory chip access opening 222 is shown in the inner wall 210 in the illustrated embodiment. A slide feed opening 24 extends through the bottom wall 22 and a small portion of the inner wall 25 (i.e., a bottom edge 26 of the inner wall is located slightly above the plane of the bottom wall).

Figure 18:
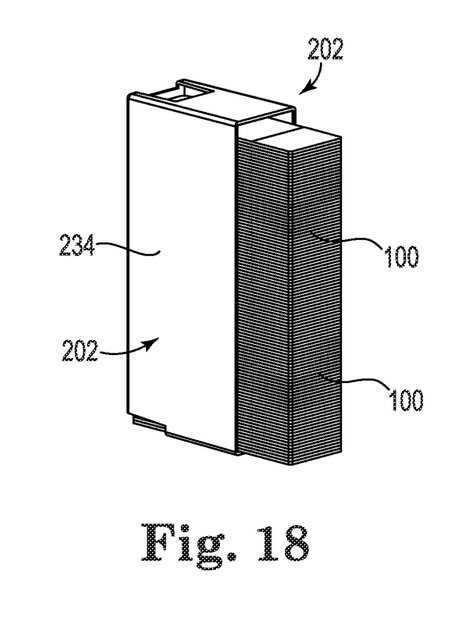
FIG. 18 is an isometric view of the slide holder shown in FIG. 15, with slides loaded in the holder.
Figure 19:
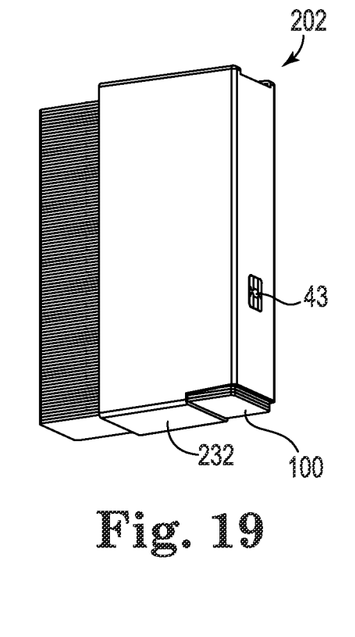
FIG. 19 is an isometric view of the slide holder shown in FIG. 15, with slides loaded in the holder.

Slide holder 202 is a generally enclosed structure that holds the slides 100. The slide holder 202 is configured to be positioned within and removed from the body 200 through the side wall 216 in the illustrated embodiment, but can be loaded into the body through other locations in other embodiments (not shown). The illustrated embodiment of holder 200 has a top wall 230, bottom wall 232, side walls 234 and 236 and inner end wall 238. A feed opening 240 extends through the bottom wall 232 and a portion of the inner wall 238. When the slide holder 202 is positioned in the body 200, the feed opening 240 in the holder is located adjacent the feed opening 24 in the body to enable slides 100 to be withdrawn from the cartridge 18 by the printer slide feed mechanism. In the illustrated embodiment, the side of the holder 202 opposite the inner wall 238 is open to receive the slides 100 and the length of the holder is less than the length of the slides to enable ends of the slides to extend from the holder (e.g., as shown in FIG. 18). In other embodiments of the invention (not shown), access to the holder for loading the slides 100 is at other locations on the holder (e.g., through the side or top walls).

Memory chip 43 is located on the outside of the inner wall 238 in the illustrated embodiment, at a location where it will be positioned adjacent the access opening 222 in the body 200 when the holder 202 is positioned in the body. The memory chip 43 can thereby be electrically connected to the connector 33 for data communications when the cartridge 18 is inserted into the printer. In other embodiments of the invention (not shown), the memory chip 43 is located at a different position on the slide holder 202.

Cartridge 18 provides a number of important advantages. Specimen slides can be handled for convenient loading into the printer while remaining free from debris. Supplies of specimen slides can be shipped in the holder, and loaded into the body by operators of the printer. The memory chip allows the printer to accurately control printer operations.

An anti-stick slide feeder 300 and associated method in accordance with embodiments of the invention can be described in connection with FIGS. 2, 10-12, 14 and 20-21. As shown, the anti-stick feeder 300 includes a high pressure gas source 302 and one or more nozzles 304. Gas source 302 is coupled to the control system 34, produces a flow of gas (e.g., in the form of a relatively short duration blast or jet) that is applied to the stack of slides 100 to enhance the ability of the input feed roller 28 to effectively and accurately remove the bottom (e.g., next-to-be-removed) slide from the stack. The nozzles 304 are positioned to direct the gas flow to locations adjacent the edges of the bottom and adjacent slides 100 in the stack (i.e., adjacent the location where the major surfaces of the bottom and adjacent slides 100 meet). In embodiments, a pair of nozzles 304 direct a gas flow to both opposite sides of the bottom and adjacent slides 100. Although the nozzles 304 produce a gas flow that is generally parallel to the major surfaces of the slides 100 in the illustrated embodiments, the gas flow is directed to the slides at other angles in other embodiments of the invention. As shown, the nozzles 304 direct the gas flow through openings 306 in the cartridge 18 in the illustrated embodiments of the invention.

Figure 20:
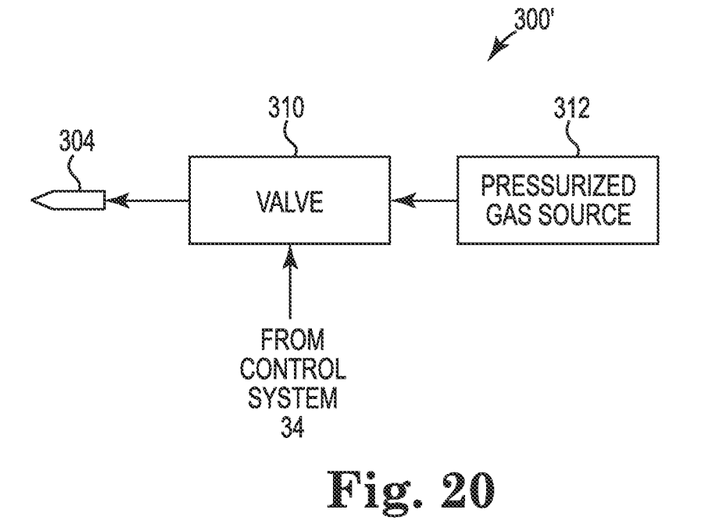
FIG. 20 is a diagrammatic illustration of a high pressure gas source in accordance with an embodiment of the invention.
Figure 21:
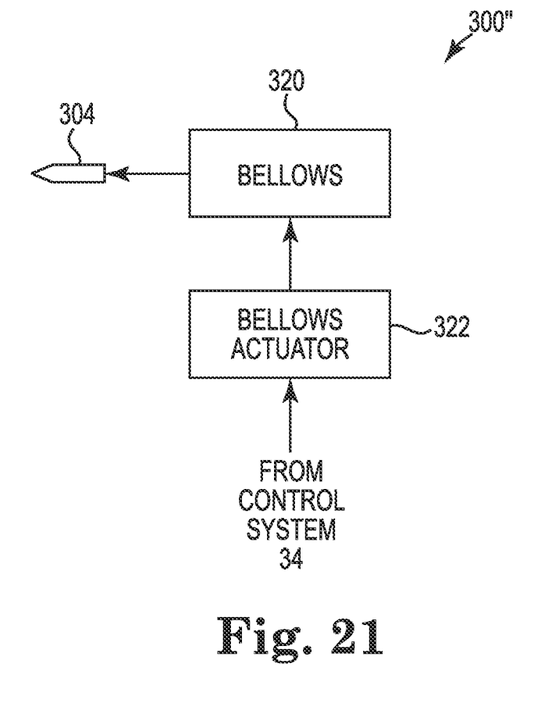
FIG. 21 is a diagrammatic illustration of a high pressure gas source in accordance with another embodiment of the invention.

FIG. 20 is an illustration of a high pressure gas source 300' in accordance with one embodiment of the invention. As shown, source 300' includes a valve 310 coupling the one or more nozzles 304 to a pressurized gas source 312 such as a $CO_2$ cartridge or an external pressurized air source (not shown). The valve 310 is coupled to the control system 34, and when actuated by the control system causes gas from the source 312 to flow to the nozzle 304. FIG. 21 is an illustration of a high pressure gas source 300" in accordance with another embodiment of the invention. As shown, source 300" includes a bellows 320 and a bellows actuator 322 coupled to the control system 34. When driven by actuator 322, bellows 320 forces a flow of ambient air through the nozzle 304.

Control system 34 can actuate the high pressure gas source 300 before and/or during the actuation of input feed roller 28 (e.g., before and/or during the movement of the bottom slide). The flow of gas provided by the source 300 may separate the bottom and adjacent slides 100, and reduces the friction and/or capillary pressure between the bottom and adjacent slides, thereby "un-sticking" the slides during the feeding action. The reliability by which the slides 100 are removed from the stack and fed into the printing system 10 is thereby enhanced.

Although described in connection with embodiments of a thermal printer, those of skill in the art will recognize that the invention can be used with other printers and other printer components. For example, other embodiments of the invention can be used in inkjet, laser or other printers. One or more single color ink ribbons can be used instead of the multiple color panel ribbon. The printhead can be a separate printhead for each ink ribbon instead of the single printhead shown in the illustrated embodiment. Any and all of the fields of information on the slides can be printed in any desired color, and the printed color can be selected to represent information such as tissue type and source (e.g., the text and/or bar code can also be printed in color). Printing can also be done in one, two, three or more colors on each slide, with sequentially printed slides having the same or different printed colors. The printer can also be used with other slides, such as slides having a colored printing area. Other transfer mechanisms (e.g., including shuttles and rollers) can be used in addition to or as alternatives to those of the described embodiments.

The invention claimed is:

1. A method for feeding histology specimen slides from a structure supporting a stack of the slides in a slide printer, including:
   providing a stack of rectangular histology specimen slides having sides and ends, including first and second slides having adjacent major surfaces in contact with one another, wherein the slides are provided in a cartridge having a side wall, a feed opening, and a gas flow opening in the sidewall;
   removing the first slide from the stack by moving the first slide with respect to the second slide in a direction generally parallel to the sides of the slides through the feed opening in the cartridge; and
   applying a flow of gas to the sides of the first and second slides through the gas flow opening in the side wall of the cartridge and through a nozzle pointing to the sides of the slides and to a location that the adjacent major surfaces of the first and second slides contact one another when removing the first slide from the stack.

2. The method of claim 1 wherein applying a flow of gas includes applying a flow of air.

3. The method of claim 1 wherein removing the first slide includes causing the first slide to slide with respect to the second slide.

4. The method of claim 2 wherein removing the first slide includes engaging a surface of the first slide opposite the second slide with a rotating feed roller.

5. The method of claim 1 wherein applying the flow of gas includes applying the flow of gas before moving the first slide.

6. The method of claim 1 wherein applying the flow of gas includes applying the flow of gas while moving the first slide.

7. The method of claim 1 wherein applying the flow of gas includes applying the flow of gas before and while moving the first slide.

8. The method of claim 1 wherein applying the flow of gas includes applying a blast or jet of gas.

9. The method of claim 1 wherein applying the flow of gas includes applying the flow of gas through a nozzle pointing at an angle generally parallel to the adjacent major surfaces of the first and second slides.

10. The method of claim 1 wherein applying the flow of gas separates the adjacent surfaces of the first and second slides.

11. The method of claim 1 wherein removing the first slide includes removing a bottom slide from a stack of slides.

12. A histology slide printer, including:
a slide receiving structure configured to receive a stack of rectangular histology slides having sides and ends, including a first, next-to-be-removed slide and a second slide having adjacent major surfaces in contact with one another, wherein the slide receiving structure includes a cartridge having a side wall, gas flow opening in the side wall, and a feed opening to expose the next-to-be-removed slides;
a printhead;
a drive mechanism to remove slides from the slide receiving structure and move the slides in a direction generally parallel to the sides of the slides toward the printhead;
a pressurized gas source;
a nozzle coupled to the pressurized gas source to direct gas from the source to the sides of the slides, the nozzle pointing to a location at the sides of the slides and to a location that the adjacent major surfaces of the next-to-be-removed and second slides contact one another, wherein the nozzle is adjacent to the gas flow opening of the cartridge, and directs the gas to the sides of the slides through the gas flow opening of the cartridge; and
a control system coupled to the drive mechanism and the source of pressurized gas, the control system configured to:
actuate the drive mechanism to remove the next-to-be removed slides from the slide receiving structure, and
actuate the pressurized gas source and cause a flow of gas to contact the sides of the slides at the location that the adjacent major surfaces of the next-to-be-removed and second slides contact one another when the drive mechanism is removing the next-to-be-removed slides.

13. The slide printer of claim 12 wherein the pressurized gas source is a pressurized air source.

14. The slide printer of claim 12 wherein the control system causes the pressurized gas source to apply a blast or jet of gas.

15. The slide printer of claim 12 wherein the control system actuates the pressurized gas source before actuating the drive mechanism.

16. The slide printer of claim 12 wherein the control system actuates the pressurized gas source during actuation of the drive mechanism.

17. The slide printer of claim 12 wherein the pressurized gas source includes a pump coupled to and actuated by the control system.

18. The slide printer of claim 12 wherein the pressurized gas source includes a valve coupled to a high pressure gas source and the control system, and wherein the valve is actuated by the control system to control a flow of gas from the high pressure gas source to the nozzle.

19. The slide printer of claim 12 wherein the pressurized gas source includes a bellows and a bellows actuator coupled to the control system.

* * * * *